(12) United States Patent
Klein et al.

(10) Patent No.: US 11,335,146 B2
(45) Date of Patent: *May 17, 2022

(54) METHOD AND APPARATUS FOR PERSONAL PATHOGEN STATUS VERIFICATION AT POINT OF ENTRY INTO AN AREA OF CONGREGATION

(71) Applicant: OPENCLEAR, INC., Henderson, NV (US)

(72) Inventors: Mark Klein, Henderson, NV (US); Wendell Brown, Henderson, NV (US)

(73) Assignee: OPENCLEAR, INC., Henderson, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/529,086

(22) Filed: Nov. 17, 2021

(65) Prior Publication Data

US 2022/0076512 A1    Mar. 10, 2022

Related U.S. Application Data (63) Continuation of application No. 17/470,937, filed on Sep. 9, 2021, which is a continuation of application No. 17/235,449, filed on Apr. 20, 2021, now Pat. No. 11,151,820.

(60) Provisional application No. 63/013,119, filed on Apr. 21, 2020.

(51) Int. Cl.
| | |
|---|---|
| G16H 10/40 | (2018.01) |
| G16H 50/80 | (2018.01) |
| G07C 9/00 | (2020.01) |
| G06Q 50/26 | (2012.01) |
| G07C 9/27 | (2020.01) |
| G16H 40/63 | (2018.01) |

(52) U.S. Cl.
CPC ....... *G07C 9/00563* (2013.01); *G06Q 50/265* (2013.01); *G07C 9/27* (2020.01); *G16H 10/40* (2018.01); *G16H 40/63* (2018.01); *G16H 50/80* (2018.01)

(58) Field of Classification Search
CPC .... G06Q 50/265; G07C 9/00563; G07C 9/27; G07C 9/37; G16H 10/40; G16H 40/63; G16H 50/80; G16H 10/60; G16H 15/00; G01N 2469/00
See application file for complete search history.

(56) References Cited

U.S. PATENT DOCUMENTS

| | | | |
|---|---|---|---|
| 6,565,000 B2 | 5/2003 | Sehr | |
| 7,092,839 B2 | 8/2006 | Buote et al. | |
| 10,390,772 B1 * | 8/2019 | Kovacs | A61B 5/0205 |

(Continued)

FOREIGN PATENT DOCUMENTS

| | | |
|---|---|---|
| CN | 111009301 A | 4/2020 |
| JP | 2020042685 A | 3/2020 |

(Continued)

*Primary Examiner* — Dionne Pendleton
(74) *Attorney, Agent, or Firm* — Manatt, Phelps & Phillips, LLP (57) ABSTRACT

A system and system for personal pathogen status verifying allows an entity to control access to an area of congregation (AOC) at one or more points of entry (POE) is a configurable manner. In one embodiment, the system may be used for the SARS-CoV-2 virus, but may be similarly used for other pathogens.

28 Claims, 1 Drawing Sheet

(56) References Cited

U.S. PATENT DOCUMENTS

| | | |
|---|---|---|
| 10,818,379 B2 | 10/2020 | Krishnan et al. |
| 10,923,216 B1 | 2/2021 | White et al. |
| 11,151,820 B1 * | 10/2021 | Klein .................... G16H 40/63 |
| 2007/0015552 A1 | 1/2007 | Bolling |
| 2017/0073722 A1 | 3/2017 | Kanhye |
| 2019/0328915 A1 | 10/2019 | Paul et al. |

FOREIGN PATENT DOCUMENTS

| | | |
|---|---|---|
| KR | 20170108735 A | 9/2017 |
| WO | WO2011005224 A1 | 1/2011 |
| WO | WO-2021198768 A2 * | 10/2021 |

* cited by examiner

METHOD AND APPARATUS FOR PERSONAL PATHOGEN STATUS VERIFICATION AT POINT OF ENTRY INTO AN AREA OF CONGREGATION

RELATED APPLICATIONS

This application claims the benefit under 35 USC 120 and is a continuation of U.S. patent application Ser. No. 17/470,937 filed Sep. 9, 2021 that in turn claims the benefit under 35 USC 120 and is a continuation of U.S. patent application Ser. No. 17/235,449 filed Apr. 20, 2021 know issued as U.S. Pat. No. 11,151,820 on Oct. 19, 2021) that in turn claims priority under and the benefit of 35 USC 119(e) of U.S. Provisional Application No. 63/013,119, filed Apr. 21, 2020, and which is incorporated herein by reference.

FIELD

The disclosure relates generally to a system and method for verifying personal pathogen status.

BACKGROUND

Mitigation methods employed by most countries during the COVID-19 pandemic have included rules reducing close-proximity interaction among individuals (or a group of people living together) and all other individuals (or groups). These "social distancing" (also "physical distancing," and "stay-at-home") rules include limits on the size of gatherings and the minimum distance to be maintained among people. Some indoor businesses can make accommodations to adhere to these rules. For example, supermarkets can limit the number of customers allowed inside and can place markings on the floor to maintain separation in checkout queues. Other businesses, such as airlines, theaters, and restaurants, are typically not economically viable with the low loading (numbers of customers permitted on an airplane or in a restaurant with social distancing) required to physically distance their customers.

Governmental mitigation orders, recommendations, and the general fear of contracting COVID-19 has effectively shut down large segments of the economy including schools, restaurants, airlines, theaters, amusement parks, hotels, and ride sharing services.

After the rate of transmission is sufficiently suppressed by mitigation (Effective R(0) driven below 1 for long enough to achieve containment), societies worldwide will balance the economic and public health implications of relaxing mitigation orders. When a vaccine is available and widely deployed, or infections progress, to the point of providing herd immunity, economic activity can resume to the level it was before the pandemic. That time may be from one to two years after the pandemic began, and should SARS-CoV-2 mutate in a way that bypasses the protection conferred by a vaccine or previous infection, the pathogen may become a recurring long-term issue. Even in the best-case scenario with a vaccine ending the scourge, continuing strict social distancing mitigation while waiting for the vaccine to become widely available will result in many businesses, especially capital-intensive businesses such as airlines, going bankrupt. Restarting them at that future point in time, would require enormous capital and human effort. It is anticipated that most societies will relax mitigation orders before the herd immunity point is reached. During this time period, many people will continue to protect themselves and their families by shunning higher risk activities, such as flying or visiting crowded venues.

To quell the fears of customers, businesses could restrict admission to people who have recently tested negative for viral infection and/or have antibodies that indicate they have already recovered from COVID-19 and/or have received a vaccination. There is currently no known system available to allow businesses to efficiently verify customer infection status and it is to this end that the disclosure is directed.

DETAILED DESCRIPTION OF ONE OR MORE EMBODIMENTS

The disclosure is particularly applicable to a personal pathogen verification system that may be used to SARS-CoV-2 (covid-19) and it is in this context that the disclosure will be described. It will be appreciated, however, that the system and method has greater utility, such as to any other pathogens whose status can be tracked and reported for a user.

The system conveys personal infection and/or infectability and/or vaccination status at the point of entry (POE) into an area of congregation (AOC) including a building, campus, business, venue, transportation vehicle, etc. The system limits AOC entry to qualified individuals, typically those who are infection-free. Businesses who deploy the system can attract customers who are fearful of close contact with other customers of unknown infection status.

There is precedence for the efficacy of assuaging fear among customers. For example, when a passenger boards an airplane, any fear they may have about other passengers carrying weapons or explosives are assuaged by the rigor of TSA passenger checks. Without such assurance, far fewer people would choose to fly. With similar motivation, the system can be used by TSA, an airline at check-in (before arrival at the airport or at the airline's check-in counter), or another entity at airport entrances, to ensure all passengers that every other passenger boarding their flight has recently been verified as not carrying SARS-CoV-2.

In one embodiment, other verifiable personal conditions may also be an input into the entry criteria to provide safety, for example other medical personal information such as non-pathogen communicable disease information, as well as non-medical personal information such as personal criminal records.

In one embodiment, a computing device executing an app, such as a mobile phone and/or web-based application, permits a person (user) to locate a pathogen (such as SARS-CoV-2) testing facility, schedule a test, and have the results of their test returned to the system. An alternate embodiment includes a testing unit placed in the user's home or in proximity of the business AOC eliminating the need for a third-party testing lab. When subsequently attempting to enter an AOC through a POE, the user presents a QR code on their computing device, such as a mobile phone, that is scanned by the POE gatekeeper using their mobile phone or other Internet connected scanning device. A system calculated PASS/BLOCK is presented to the gatekeeper on their display device (either their mobile phone or a display device linked to their scanning device). In some elevated security cases, a rule-driven subset of information drawn from the user's test results and their identifying information (such as name, date of birth, height, driver's license number, photo, etc.) is presented to the gatekeeper.

Each POE may have a set of verification rules. For example, rules for a particular POE may require that identification (driver's license, etc.) be presented that matches the test results. For some POEs, a code will be presented to the gatekeeper and the same code will be sent to the user via SMS or through the application. The user must then say the code or show it to the gatekeeper to confirm the QR code is displayed on the device on which it was generated. AOE and/or POE specific rules are executed by the system to control entry and other enhanced security features (see further description under the Usage at Point of Entry section below).

Note that an AOC may have multiple POEs. The rules may differ among POEs. For example, employees may enter through one set of POEs and customers may enter through other POEs. The POE rules for employees may be different than POE rules for customers. Rules may differ for different classes of users passing through the same POE. The system can apply different entry criteria rules when an employee or a customer is attempting to pass through the POE.

The testing criteria for a POE can vary depending on the risk associated with the AOC on the "clean side" of the POE. For example, the risk of infection may be higher during a 12-hour flight on a fully loaded Airbus A380 than the risk of infection at a typical restaurant. The system and method execute AOC specific rules that are stricter for higher risk AOCs. For example, to enter an airport, or to board a 12-hour flight, a rule may require a negative SARS-CoV-2 test within 3 days. To enter a restaurant or sporting event, or to board a 1-hour flight, a less restrictive rule may require a negative SARS-CoV-2 test within 5 days. The risk and resulting rules for an AOC can be determined by epidemiological study. An entity managing an AOC may set rules more restrictive than epidemiological or governmental orders/recommendations should they deem it advantageous in the attraction of customers, protection of employees, or for other reasons.

The system retains a history of operational events that can be used for auditing, governmental reporting, epidemiological study, regulator reporting, and other purposes.

The system can be used at the openings in physical boundaries (POEs) around an AOC or it can be used in conjunction with an existing ticketing/pass-generating system (ticketing system) through an electronic (or other) integration between the system of the invention and the ticketing system. One example of the operation of such an integration would be when a ticket is scanned at a POE, the ticketing system can make a real-time query to the system of the invention to confirm the user is qualified to enter. This query can be keyed by the user's telephone number or other unique identifier known by both the ticketing system and the system of the invention.

AOCs for which the system can be used may include spaces with no other people present, for example spaces that must be maintained virus free, such as medical labs, clean rooms, and delivery vehicles. This use case can be supported by the system without a gatekeeper, instead using a manned or unmanned scanner at the POE. A system-controlled AOC can include a person's vehicle, in which case the owner of the vehicle would verify the negative test status of the mechanic they employ to work on their vehicle. This use case can also be implemented by the shop providing mechanical services that employs the system to periodically (manually or automatically using a system provided employee status dashboard) confirm the status of their employees allowing them to advertise the virus-free status of their workers. The employee status dashboard can be used to identify employees out of compliance and to prompt employees to complete testing. This system use case is not limited to repair shops and can be applied to any business with employees who occupy spaces or handle objects belonging to customers, or to be used by customers (rental cars, for example).

The system can be used by individuals to mutually confirm each other's status (two or more individuals) when meeting in public or in private. This confirmation can be performed using the scan of each participant user's mobile phone displayed QR code by another participant. The confirmation can also be performed by a $3^{rd}$ party system, such as a dating website/application. The system can be used socially among friends. The system can be used for transactional meetings among erstwhile strangers such as between someone hired to visit a home (plumber, handyman, appliance installer, house cleaners, babysitter, etc.) and the resident.

AOCs for which the system can manage POEs include, but are not limited to, airplanes, airports, restaurants, transportation vehicles (for passengers and employees), buildings, schools, campuses, geographic regions (cities, counties, states, countries, etc.), hotels, lodging rentals (for example VRBO and Airbnb), retailers, ride sharing services, delivery services (including parcel and on-demand food and product delivery), convention centers, concert/show venues, theaters, sporting event venues (stadium, gymnasium, etc.), warehouses (employees and visitors), hospitals, nursing homes, cruise ships, festivals, repair shops, veterinary clinics, doctor's offices, dentist's offices, hair/nail salons, massage parlors, amusement parks, and casinos.

In all cases, users (in the role of a passenger, customer, participants, etc.) and AOC agents (typically employees or contractors) may be qualified by the system. Rules for users and for AOC agents may be different and can be set by the entity managing the AOC specific to the class of person to be admitted or the POE through which they enter the AOC.

In a restaurant use case, a restaurant can use the system to offer a "clean night" where only verified negative status individuals are permitted entry. The system can be used at the front door of the restaurant (POE), or integrated with the restaurant's reservation system (for example, OpenTable or Yelp). In a ride sharing use case, a ride sharing service's driver and passenger(s) may exchange verifications before initiating a ride that may happen at pick-up time or through electronic integration when the ride is scheduled. A business (restaurant, theater, concert venue, sporting event, hotel, etc.) may offer classes of occupancy such as, "immune," "verified negative," or "open." The system would be deployed at POEs surrounding all but the "open" area.

The use of the words "test" and "testing" in this application should be construed to include the confirmed execution of other medical procedures, such as vaccination. It should also be construed to include medical conditions and genetic markers making a person more or less susceptible to infection. It should also be construed to include self-reported health history and current status, including the presence or absence of specific symptoms. The system therefore can convey the test results for the presence of pathogens, test results for the antibodies against pathogens, a user's vaccinations against pathogens, and other qualifying or disqualifying information. The system can support a multitude of test results along with a user's vaccination and health history.

The system can be employed at geographic borders to qualify a user's entry into a controlled area. In the case of International borders, vaccination status has typically been conveyed using a paper International Certificate of Vaccination. The system can replace the International Certificate of Vaccination allowing more accurate, and rapid checking at borders. The system can be employed at time of entry, by an airline (or other International transport service) at check-in, by a pre-arrival visa issuing agency, or by other means.

Figure 1:
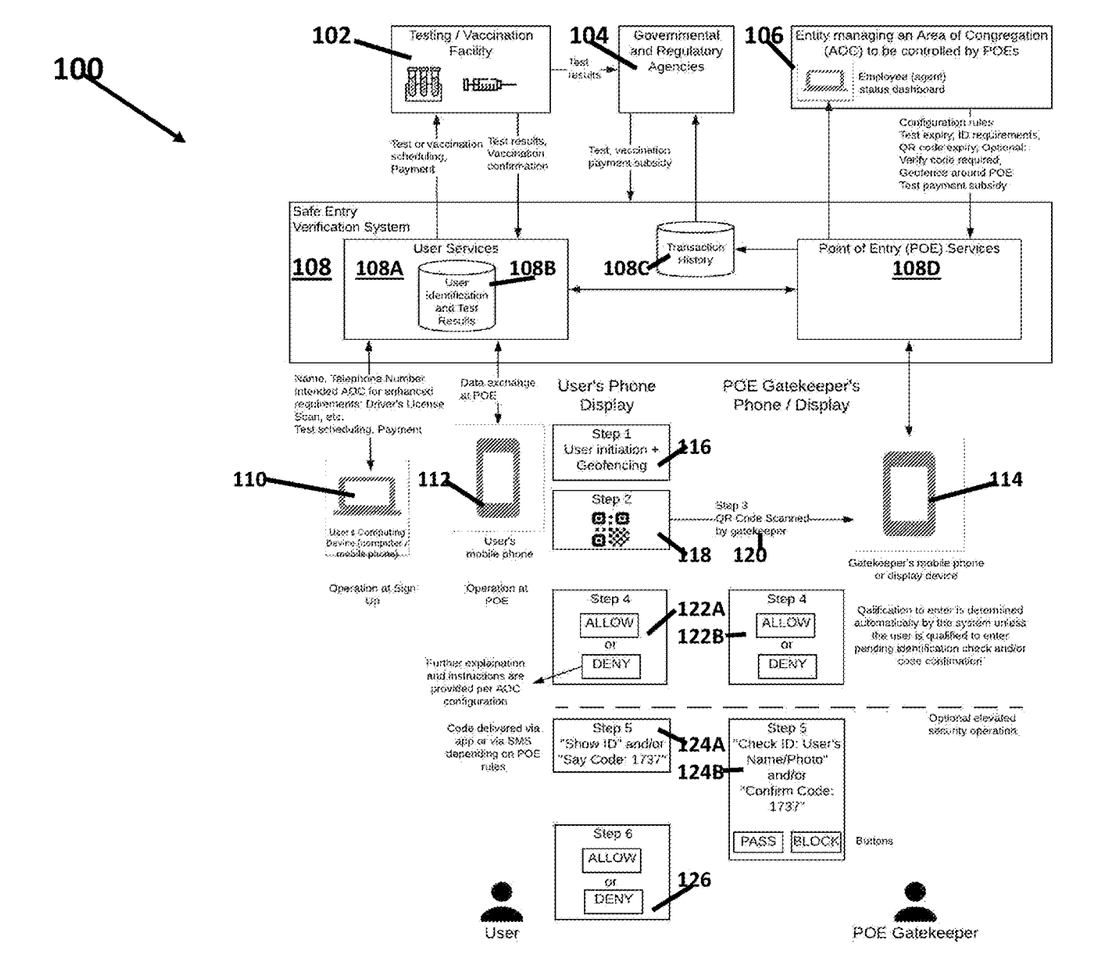
FIG. 1 is a diagram showing an implementation of a personal pathogen status verification system and method for personal pathogen status verification.

FIG. 1 is a diagram showing an implementation of a personal pathogen status verification system 100 and method for personal pathogen status verification. The system may include one or more testing/vaccination facilities 102 that can schedule a test or vaccination for a user and receive payment and communicate the test/vaccination results (or a confirmation of status) to one or more parties who are part of the system 100. As shown in FIG. 1, the parties may include, in some embodiments, a user who wishes to access an AOC through a POE one pathogen status is verified, a POE access employee (gatekeeper), the entity that manages the AOE and the one or more POEs and government or regulatory agencies 104. As discussed above, for certain embodiments, a gatekeeper may not be used such as when accessing a secure location inside of a company. The entity 106 managing the AOC to be controlled by one or more POEs may have a status dashboard that shows its employee/agent status. Furthermore, each entity 106 may provide configuration rules that govern how the pathogen status verification system operates for the particular entity as discussed above.

The system 100 may further include a safe entry verification system 108 that communicates with the testing/vaccination facilities 102, the government agencies 106 and each entity 106. The safe entry verification system 108 (and each of its elements) may be implemented as one or more computer systems (server computers, mainframes, blade servers, etc.) or cloud computing resources that has at least one processor and memory that stores a plurality of lines of computer code/instructions that are executed by the processor so that the safe entry verification system 108 (or the at least one processor) is configured to perform the processes and operations of the safe entry verification system 108 discussed below. The safe entry verification system 108 may include user services 108A that has a database 108B that contains user identification and test results wherein the user services 108A communicates with each test/vaccine facility 102. The safe entry verification system 108 may have a transaction database 108C that communicates data from the safe entry verification system 108 to the agencies 104. The safe entry verification system 108 may also have a point of entry (POE) system 108D that provides POE services and is connected to the user services 108B, the transaction history database 108C and each entity 106. Thus, one operation performed by the POE system 108D is to configure the POE operation for each entity 106 based on the configuration and provide POE data to the entity 106 to display on the dashboard.

Sign Up and Testing/Vaccination

A user who wishes the gain access to a particular AOC by an POE may sign up for the system and its services using a computing device 110 (such as a mobile device, smart phone, phone, desktop computer, laptop computer, tablet computer, etc.). The user signs up for the service, typically motivated by their anticipated entry into a specific AOC. The user specifies the AOC (if any) and the system displays the requirements for entry into the AOC. The user schedules the required tests and/or vaccinations through the system (or outside of the system either by referral from the system, or by other means) and supplies necessary identifying information. Payment can be made through the system or directly to the testing/vaccination facility. Some businesses, such as airlines, may subsidize testing for their customers. A governmental agency may also implement subsidy programs. The system can settle both types of subsidy. Test results are returned to the system by the testing facility either through electronic integration with the facility's system(s), through electronic integration with the testing equipment in use at the facility, or by manual reporting using the system provided test facility portal. In a similar fashion, vaccination confirmations are reported to the system by a vaccination facility.

The test results from the facility 102 are matched to the user. If the system scheduled the test, this matching is performed by test order number (generated by the system or by the testing lab). Further confirmation is made by matching name, telephone number, social security number, or other identifying information. If there is no electronic integration with the testing facility (whether or not the user scheduled a test through the system), then the test may be imported by scan/photograph, by manual ($3^{rd}$ or $1^{st}$) party entry, and matching a test result to the user is performed by confirming as many user identifiers and test result identifiers as are available. These identifiers include username, address, telephone number, social security number, GPS location at time of test, age, gender, TSA KTN (Known Traveler Number), and other identifiers. If the testing was prompted by the user's intention to enter a specific AOC, an AOC generated identifier may also be associated with the user and/or the test. For example, an airline reservation number. In some use cases, the system automatically forwards test results to the AOC where it can be used to issue a ticket or permission to enter within an AOC defined time period. The system confirms manually entered test results using anti-fraud imaging techniques, automated or manual phone calls for verification, and other methods.

In the preferred embodiment, the system retrieves test result by collecting testing facility credentials from the user and acting as their proxy to sign into their account with the testing facility to simulate the manual retrieval of test results. The system performs this operation using software located on one of a set of servers or from the user's mobile phone. The retrieval can follow prescribed web navigation paths to locate the test result or it employs Artificial Intelligence techniques to locate the test record. In some cases, the user will be prompted to guide the system to the test results and the system will "learn" from this guidance. If the testing center reports results to a centralized agency, such as a state health department, the system may interrogate the agency's database to collect test results instead of, or in addition to, the testing center. The test results are parsed to extract the minimal information necessary for system operation thereby maximizing user privacy. The pertinent portion of test results are encrypted during storage. An alternate embodiment includes a Personal Testing Unit (PTU) that can be placed in a person's home or in proximity of a business AOC eliminating the need for a third-party testing lab. In this embodiment, the system associates test results with the tested person. Test results from the PTU are moved to other components of the system via the scanning of a matrix barcode (QR code, etc.), Bluetooth, Wi-Fi, or another conveyance method.

Usage at a Point of Entry

When approaching a POE of an AOC, the user may use a computing device 112 (that may be the same as user previously or a different mobile phone) and opens the mobile phone application (associated with the safe entry verification system 108). A personal time-limited unique code (118) is displayed in the application. The unique code may be a QR code in one embodiment, but may be any other code/image/ display (including, but not limited to, a barcode, matrix barcode, or a custom two-dimensional barcode) that accomplishes the same result of providing the user's test/vaccination status at the POE. If a geofence was specified (116) by the entity managing the AOC, a QR code that is restricted for use at that POE/AOC will be displayed instead of the user's more generic personal QR code. If there is a unique QR code for the POE, then The generic QR code is not valid for this POE which is an optional enhanced security measure.

The gatekeeper scans the code (120) using a scanning device 114 (such as a mobile phone or other scanning device, or any mobile phone with a camera that supports QR code to browser URL execution is sufficient) of the gatekeeper. In the simplest case, the system displays an ALLOW or DENY message 122A, 122B on the gatekeeper's device 114. The result is also displayed on the user's device 112. Under more restrictive AOC rules, further confirmation must be made by the gatekeeper. Instructions are displayed on the gatekeeper's device 114 (124B) and the user's mobile phone (124A). If the rules require an identification confirmation, the user's name (and if specified by AOC rules, a photo or a redacted scan of their driver's license or other ID) is displayed for matching against their physically presented ID. Optionally, a rule can require a real-time confirmation that the QR code displaying mobile phone belongs to the user. This is performed by sending a code to the application (or via SMS) to the user's mobile phone. The gatekeeper is also shown the code on their mobile phone. The gatekeeper confirms identification and/or code match and selects "PASS" or "BLOCK" depending on the identification and/or code confirmation. If "BLOCK" is mistakenly pressed by the gatekeeper or if the user misspeaks the code, the entire transaction can be repeated. The system provides an optional mobile phone application for gatekeepers to streamline the scanning process.

In use cases that require the gatekeeper to check a user's identification beyond name match, a photograph may be displayed on the gatekeeper's mobile device. This photograph, used for visual identity confirmation, can be extracted from public records, such as a DMV database or it can be uploaded by the user by scanning their driver's license or other identification document. Other identifying attributes of the user may be displayed to aid the gatekeeper such as age, height, weight, etc.

In some embodiments, the system 100 executes AOC specific rules that are stricter for higher risk AOCs. For example, to enter an airport, a rule may require a negative SARS-CoV-2 test within the past 3 days, and to enter a restaurant a rule may require a negative SARS-CoV-2 test within the past 5 days. When passing through a POS, the system application informs the user of the entry criteria in effect inside of the AOC allowing the user to take any enhanced precautions they deem necessary.

In cases where the system is used without a formal AOC, individual users are able to present their personal QR code and to scan each other's QR codes. In the preferred embodiment, this use case displays results on the user's mobile phone and not on the scanner's mobile phone. The scanner will get confirmation that the scan completed along with a notification to look at the user's mobile phone for results. This is to enhance privacy and prevent the scanner from screen grabbing the user's test results. In this use case, the user's first name, pertinent test results, and date/time of testing are displayed. One use case for this mode of operation is the exchange of sexually transmittable disease test results.

Throughout this application the viral pathogen SARS-CoV-2 and the disease it causes, COVID-19, are used as currently pertinent examples. Alternate embodiments of the system 100 include any testable pathogens and the diseases they cause along with any vaccinations against any communicable diseases.

The tests described in this application may be performed using qPCR, nucleic acid detection, or any other method known now or developed in the future that detect viral, bacterial (or other) pathogens present in a user's body. Also included are tests for the presence of antibodies that might confer immunity to the user. Acceptable specific tests (type of test, machine used, reagents used, number and location of viral RNA regions targeted, etc.) and result thresholds can be specified by AOC/POE configuration rules.

In an alternate embodiment, other methods of communicating between the user's mobile phone and the gatekeeper are employed, including Bluetooth communication, SMS exchange. In another alternate embodiment, the user is identified through biometrics (or other means, with or without a mobile phone) at the POE.

The system supports use cases requiring recent negative virus test results, and/or positive antibodies test results and/or vaccination and/or personal genetic markers, and/or personal characteristics including pre-existing conditions, and/or detected travel outside (or inside) a set of geofenced areas. Flexibility is designed into the system to anticipate unforeseen use cases that include different combinations of test results, vaccinations, and personal characteristics (such as genetic markers and health conditions) that can be calculated to determine suitability to pass through a POE. For example, the presence of antibodies does not exclude the possibility of the presence of the virus because antibodies are detectable before the end of infection. However, if admission is limited solely to users with antibodies, it is unlikely any new infections will take place in the AOC.

In an alternate embodiment, entry into an AOC can be detected by passing through a boundary defined using a location-based geofence (using GPS, WiFi, Bluetooth, audio signal matching, or other methods). When a user passes through boundary (virtual POE), the system automatically detects the event and notifies the user and/or the entity in control of the AOC, and/or other users already inside the AOC of the pathogenic status of the user. In some use cases, the criteria for entry may allow users with a wide range of test result statuses to enter. For example, any user who has been tested in the past two weeks may enter. However, other users inside the AOC will be notified when users approach them (based on Bluetooth signal, GPS, ultrasound ranging, or other proximity determination methods). If the approaching user does not meet the pre-configured criteria of the approached user, the system can notify one or both users. An example of this use case is the sparse congregation that takes place on a wilderness trip (hunting, camping, etc.) or the denser congregation of a music or art festival.

In an alternate embodiment, AOCs may be grouped (sequentially or in an arbitrary order). The system manages the entry criteria of a POE into one or more of the grouped AOCs so the entry criteria of every AOC is met. The system tracks the user's location, or detects if they leave (or enter) a set of geofenced areas and this history is considered by the POE/AOC rules. For example, in the case of an international flight with an airline (or other flying regulatory agency)

requirement of a negative COVID-19 test in the past 3 days and the destination country with a positive antibody test the system would require both conditions be met before clearing a person to board the flight. In another example, a packaged promotion consisting of a flight to Disneyland requires a negative COVID-19 test within 3 days and that the user take approved transportation, stay on the Disneyland property (or another access-controlled property) for the duration of time between arrival and departure for the return flight. The system tracks the location of the customer during their stay, and if they leave the controlled region (Disneyland, access-controlled lodging) or take non-approved transportation to or from the airport, they would fail the entry requirement for the return fight. Another example is a ride sharing service with a destination with system controlled access (a hospital or museum). The scan at pickup (or system query at ride booking time) considers the entry requirement of the ride destination before scheduling the ride.

In an alternate embodiment, the system displays, in addition to the QR Code for POE, a QR Code (or other machine or human readable) entry ticket (for a flight, concert, etc.) to simplify and speed processing at the POE.

In an alternate embodiment, the system can accept test results from printed (or electronically displayed) test results by scanning/photographing the printed result, using OCR (or human transcription) to extract the information, and verify the result electronically or manually.

In an alternate embodiment, the database 108B containing test results in FIG. 1 can be located in an external service, such as an AWS HIPAA compliant datastore. Access to test results can be done using hashed keys in a manner that retains overall system HIPAA compliance.

In an alternate embodiment, when the user initially signs up on (or starts) the system application and/or when they import test results, the system collects one or more user biometrics (thumbprint, iris scan, photograph using the selfie camera or another method). These biometrics can be confirmed by the system, if required by POE/AOC rules, when the system generates a QR Code for POE/AOC access. In addition, or instead, the system application can present the photograph for gatekeeper inspection either on the user's mobile phone with the QR code (before or after scanning by the gatekeeper) or on the gatekeeper's display device.

In an alternate embodiment, the system can optionally operate without a user application. The gatekeeper initiates a challenge/response cycle with the system employing a unique user identifier, such as the user's telephone number, or a customer record identifier indexing a record containing the user's telephone number. This challenge can be initiated with a text message (or other method) to the system containing the query request directly by the gatekeeper or through their point of entry/ticket reading scanner system. The system of the invention sends a confirmation SMS text to the user. If the user responds in the affirmative, the system-calculated result is returned in the response to the gatekeeper. In practical operation, the gatekeeper scans the boarding pass/concert ticket, etc. and the POE/AOC system queries the system of the invention. The user receives a text requesting authorization to release their health record. When the user authorizes the release of the health information via confirming text reply, the system transmits the rule-calculated result to the POE/AOC system. In the 'pass' case, the user's entry would be allowed.

A virtual POE may correspond to a physical entry point such as a doorway into a building or a gate into a fairground. An agent of the AOE may be stationed at a physical entry point to confirm all persons who pass are users of the system. Confirmation can be made by physical inspection or the system can automatically determine when a user is passing a virtual POE and send notification to the POE/AOE. The notification could be used to unlock a physical turnstile allowing the user to enter.

The system provides an ancillary benefit to society by motivating widespread testing among asymptomatic individuals allowing for early detection, treatment, and isolation. The system permits the efficient filtering of people into a controlled area based on the results and elapsed time from pathogen tests and vaccinations. This filtering increases confidence for all users in the safety of entering the controlled area. The system can be deployed to assist in restarting and continually operating businesses that require serving groups of customers in close proximity with each other and/or with agents of the business.

The disclosed system and method may provide a method of protecting individual privacy while restricting entry into an area based on the individual's condition as detailed a above. The system may also provide coordination of entry based on medical information prior obtained about an individual or by a wireless electronic device.

The system and method allow a user to demonstrate that the user is a low risk for spreading the disease (vaccination, by recent negative test). The AOC may be a vehicle, vessel or group and may provide time limited access though a POE to the AOC. In some embodiments, the user could use a biometric confirmation step (using a fingerprint sensor on his mobile device or other biosensor—iris for example or voice) to confirm that he is the same person (as confirmed by his biometrics) that the displayed/presented medical information/record is about. Alternatively, for privacy, the user may show a redacted driver's license—enough to properly identify the person (picture/name) but redact private info (address, birthdate, etc.). The system and method may also confirm that the target user's device is in fact belongs to that user using a method of challenge/response, which can be one or more steps.

The system further provides a method of coupling the result of a medical test (or medical information such as vaccination) to the person/phone number/sim #/IMEI # of the computing device of the user and/or to couple that person's medical record (received/retrieved from a medical testing outputs) can be associated to this user by one or more methods of: Phone number, SIM # match, Name match, KTN (known traveler number/used by TSA/airlines) number, Passport number/clear account number and/or matched via a visual picture. For matching with a visual picture, facial photo recognition (matching the face of the person that was presented to the testing lab/match that face to the face on the driver's license and/or match to the face as viewed by the user's mobile phone camera and/or match to the face as presented to the challenger's image input system such as an airline agent's personal mobile phone, an airport gate entry system (operated by TSA/Clear/an airline), etc.) may be used. The matching may occur via a matching facial image/recognition (matching the facial image that was presented at the place/time that the medical test was given, then matching that at the time/point of entry to the restricted area). Furthermore, the system may match via a matching voice print recognition (again, matching the voice that was presented at the place/time that the medical test was given, then matching that at the time/point of entry to the restricted area) or perform matching via an image of the front or rear (sometimes a scannable bar code) of that user's driver's license or passport (again, matching the info that was presented at the place/time that the medical test was given, then matching that at the time/point of entry to the restricted area).

The system and method may use a wearable item (bracelet, watch, smartwatch, ID tag etc)—worn on the wrist/leg/ or otherwise on the body), or implanted into the user's body, for matching that contains a hologram/image/RFID chip or other electronic or optical or radio means of identity as used for purposes of entry, as described herein, based on that user's prior medical information (vaccination info, negative test result info, or other info).

The architecture as shown in FIG. 1 may include one or more hash function to be able to identify the user or medical record, while enhancing privacy. Furthermore, the architecture as shown in FIG. 1, with one or more data elements stored in an external (or the cloud) $3^{rd}$ party solution (e.g. Amazon AWS cloud service or similar), that is HIPAA compliant (Health Insurance Portability and Accountability Act of 1996, commonly known as HIPAA), whereby personal info and/or medical information is stored in the $3^{rd}$ party HIPAA compliant data store, with associated hashed data/indexes which correlate/link the external personal ID information, with the internal HIPAA-protected personal/medical data, with the goal of keeping the personal information and medical information inside the HIPAA protected data storage, while allowing external access (input: one or more identity info of this user, input: criteria of information requested, output: one or more of pass/fail or finer detail (for example this person most recently had a negative test a predetermined number of days ago).

In one example, the user may input a UniqueUserID, criteria and receive a Yes/No result. The UniqueUserID may be created when the user signups (via mobile or web etc) and user would extend an existing account and the uniqueID is either created, or referenced to a prior uniqueID, associated to a new user signuped uniqueid, associated with one or more prior uniqueID. An open API may be used which inputs any of a number of uniqueID (or references a prior uniqueID—AA loyalty, United loyalty number, etc.). For example, a user books a flight, just to make a reservation, my flight reservation is prior linked to my unique ID. Then at a later time, but before entry time (for example, before a boarding pass is issued which is usually has to be within 24 hours of flight), the user has to make a final verification of valid medical information which meets the criteria for this entry. For example, for a plane flight, a policy may be set (by the airlines, government, unions, local laws, etc) that requires a person (the person flying) to have a defined medical test that is valid within a predetermined number of hours/days prior to boarding this flight. That person could, for example, reserve his plane flight one month in advance, would be advised of the requirement /type of test/ for that specific flight, the person could book that flight reservation, but that person's ability to actually board the flight (or check-in luggage, or be issued a paper or electronic boarding pass, or other prior step) would require the successful verification that the required step or steps (getting a medical test a predetermined number of hours/days prior to entry/boarding) would need to be verified.

The disclosed method of verification of medical test/vaccination may be received by use of a link or pointer (as represented by a scannable QR code, link, or other audio/electronic/visual/radio or other representation form) to that person's actual medical information. For example, a user who wishes to fly may visit a medical location (e.g. doctor's office, CVS, Walmart, or other store) to get his test. That person is that given a link (a QR code, link in a text or email, a printed receipt with that link/QR code/receipt number etc) on it, which provides a link to that person's test result (or vaccination) information. The challenger (airline/restaurant/hotel/cruiseline/concert venue/entertainment facility/Disney park/school/etc) then scans/enters/accesses that link (given from the user who got test, to the challenger) who can then (from the challenger's mobile device or fixed equipment) see all or limited information resulting from that test/vaccination, along with identifying information (i.e. person's picture), along with criteria information (yes this test was given meeting some form of criteria—e.g. test was completed with the most recent predetermined number of hours/days/weeks/months/years). Using the method, the challenger can quickly/easily verify that the person presenting himself for entry has, in fact, met the criteria for entry). One or multiple types of identify/photos could be shown—for example a photo of a user could be uploaded by himself, but another photo could also be taken by the testing facility too, thus one or more photos could be shown to the challenger, or used by this invention to verify that the same person presenting himself for entry, was, in fact, the same person who was tested/vaccinated, by use of facial photo comparison/recognition, or other matching.

A bi-directional method of two mobile devices facing each other may be used, with visual information (such as a QR code) presented by device A, which is then seen/viewed by device B's front facing camera, then the opposite also: visual information (such as a QR code) presented by device B, which is then seen/viewed by device A's front facing camera, as a method of challenge/response.

The disclosed system provides a method of linking, storing, or accessing personal medical information (vaccination history, recent medical test result information), via one or more direct/indirect links or associated, via an online service (such as a social network like Facebook, a travel service like Expedia, etc) which is used as a shared account in order to store or transfer anonymized (e.g. hashed or other similar techniques) links or pointers to medical data (which may be stored in yet another location), but automated access by the "entry point" challenger. For example, a user may store his CVS customer number or a hash of his CVS customer number (or other identifying information) on my profile at Expedia (or a specific airline), or Facebook. The user then visit any CVS which then inserts my most recent test into my personal CVS record. Automatically, prior to my flight, my airline (or via Expedia or Facebook etc) would access my most recent medical test information, indirectly via one or more linkages, such that the airline automatically has access to my most recent test information, as provided by the one or more links that the user has provided.

The system further provides a method of automatically searching my one or more provided associations/links/pointers to my medical data, with the specific search criteria being my "most recent" test result which meets the input criteria. The system further provides a method of associating medical record(s) to the user using one or more scans (QR codes), email links, second factor methods, facial or other biometric association, phone number/SIM #/IMEI # or other hardware item identifiers (wearable ID # such as an apple watch ID # or fitbit ID #), such that the test provider scans/links/associated the information associated with a test, to the user or the user's device. The system further provides a method of associating medical record of the user to the user by means of one or more physical cards (such as an existing credit card, credit card magnetic stripe, credit card chip EMV/RFID, RFID chip, passport with an embedded RFID chip, etc), with at least one other type of associating information on that card (such as a picture of the user). The system further provides a method of associating the medical record of the user to the personal mobile device of the user, by means of biometric verification, hashed data stored in my phone, associated to a TPM of hardware (laptop) device, SIM #, IMEI #, secure enclave area of my mobile device, etc.

The system further provides a method of associating a person's medical data, as direct data or associated/linked data that is stored or linked or processed, in any form, by a mobile device's secure enclave area. With Apple's Secure Enclave and ARM's TrustZone, the Secure Enclave or TrustZone is not technically a different "chip." Instead, it's a separate, isolated processor built into the device's main system-on-a-chip. While it's built-in, it still has a separate processor and area of memory. Think of it as a chip inside the main chip. Either way—whether it's Titan M, Secure Enclave, or TrustZone—the chip is a separate "coprocessor." It has its own special area of memory and runs its own operating system. It's completely isolated from everything else. In other words, even if your entire Android or iOS operating system was compromised by malware and that malware had access to everything, it wouldn't be able to access the contents of the secure area.

The system further provides a method of associating a person's medical data, as direct data or associated/linked data that is stored or linked or processed, in any form, to a method of payment (such as ApplePay), or to groups of payment methods. For example, if a user used a payment method (for example ApplePay) to pay for the medical test of the user, then the user used that (or a related method of payment) for my ticket purchase (airplane fare, concert purchase, movie ticket, etc.), then the medical test result of the user would be automatically linked to that entry point (onto the airplane, into a movie theater, etc), allowing a person to coordinate his medical information in a low-friction, automated means. In another embodiment, the user uses a VISA card to pay for the medical test (or the VISA card is associated with the CVS account, and the user gets the medical test at CVS), then the user could use a different but associated credit card to purchase/verify the point of entry of the user. The user's multiple payment methods could be "coupled" through the multi-bank memberships of the VISA credit card community, such that the user can use one VISA card to pay for the medical test, yet use a different VISA card to buy a movie ticket. In this case, VISA would act as a $3^{rd}$-party to associate the medical test information paid for by one VISA card with the entry authorization paid for by a separate VISA card. Other $3^{rd}$ parties, for example credit bureaus (for example Equifax) could also act to associate different forms of payments to the medical information of the user as well. The user could associate (for example all of the various credit cards) to all be associated with the medical information, for purposes of matching/storing/accessing the medical information.

The system further provides a method of linking personal medical test information (test results, vaccination history, etc) of the user with government or other entity issued identity (passport, driver's license, social security card, DOD identify card, RFID card, Disney parks bracelet)—paper, passport number, passport RFID chip, etc. Thus, when the user wants to enter an area (into an airport, airport building, airport gate, airplane etc. or enter into Disneyland) the identity of the user (as issued by the government or other entity) is presented in order to link/access to associated medical information. Such medical information could be stored in/on the identity presented itself, or linked to medical information which is housed/stored in another location (in the cloud or other location).

The system further provides a method of additional/further verification (that this person is the same person who got tested/vaccinated) by means of matching facial recognition, voice print matching, Personal identity number (PIN) verification, biometric matching (fingerprint/IRIS/etc.), personal equipment (mobile device) identity information, challenge/response test or a serial of questions (what is your mother's maiden name, which street do you live on in 1995, etc.), challenge/response based on the questions/answers in my personal credit report, challenge/response based my financial transactions/information or account information, challenge/response based on my physical behaviors (the style/force/speed, arcs/tendencies of how the user interacts with my mobile phone), the personal written (on a digitizing pad) of a written signature style, passwords known to the user, and other second-factor methods etc.

The system further provides a method of additional/further verification (that this person is the same person who got tested/vaccinated) by means of matching instant DNA data of the user with the DNA data prior obtained or referenced. The biometric confirmation could be done on my personal mobile device (mobile phone), or by a challenger's equipment (for example a fingerprint scanner at an airport gate, and/or associated with a fingerprint scanner at the medical test provider).

The foregoing description, for purpose of explanation, has been with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include and/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general-purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software, and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

What is claimed is:

1. A method, comprising:
providing a safe entry verification system comprising a point of entry system, wherein the point of entry system is disposed at an entry of an area of congregation having one or more points of entry and wherein the safe entry verification system is configured to receive a result of an analysis of a medical condition of a user related to a pathogen;
releasing the result of the medical condition analysis to the safe entry verification system, wherein the release of the result of the medical condition analysis to the safe entry verification system is authorized by the user on a computing device; and
determining, using a computer system of the safe entry verification system at a particular point of entry, entry of the user into the area of congregation based on the result of the medical condition analysis.

2. The method of claim 1, wherein determining entry of the user further comprising denying access to the area of congregation though the particular point of entry when the result of the medical condition analysis does not meet an entry requirement and granting access to the area of congregation though the particular point of entry when the result of the medical condition analysis meets the entry requirement.

3. The method of claim 2, wherein the medical condition analysis is a pathogen test and the entry requirement is a negative pathogen test.

4. The method of claim 3, wherein the entry requirement is a negative pathogen test within a period of time of entry into the area of congregation.

5. The method of claim 2, wherein the medical condition analysis is a vaccination and the entry requirement is a completed vaccination.

6. The method of claim 2, wherein the medical condition analysis is a test of an attribute of the user.

7. The method of claim 6, wherein the attribute of the user is a genetic marker.

8. The method of claim 2, wherein the medical condition analysis is a test for one of an absence or presence of a disease.

9. The method of claim 2, wherein determining entry of the user further comprising performing a rule-based interpretation of the medical condition analysis result to determine the entry requirement.

10. The method of claim 2, wherein determining entry of the user further comprises verifying, by the safe entry system that controls the particular point of entry, an identity of the user using identifying information of the user.

11. The method of claim 10, wherein the user identifying information is one of a name of the user, a photograph of the user, a fingerprint of the user and a facial scan of the user.

12. The method of claim 1, wherein the area of congregating is one of a building, a vehicle and a venue.

13. The method of claim 1, wherein authorizing the release of the result of the medical condition analysis further comprises presenting, using the computing device of the user, a QR code at the particular point of entry.

14. The method of claim 1, wherein authorizing the release of the result of the medical condition analysis further comprises sending, using the computing device of the user, a confirming SMS text at the particular point of entry.

15. A system, comprising:
a safe entry verification system, having a computer device, that controls access to an area of congregation having one or more points of entry, wherein the safe entry verification system comprises a point of entry system disposed at each of the one or more points of entry;
wherein the point of entry system determines if a user gains access to the area of congregation;
wherein the safe entry verification system receives a result of an analysis of a medical condition of the user related to a pathogen from a medical analysis facility, wherein the user authorizes the release of the result of the medical condition analysis to the safe entry verification system; and
wherein the point of entry system at a particular point of entry of the area of congregation is configured to determine entry of the user into the area of congregation based on the result of the medical condition analysis.

16. The system of claim 15, wherein the area of congregation is one of a building, a vehicle and a venue.

17. The system of claim 15, wherein the point of entry system at a particular point of entry is further configured to read a QR code presented on the computing device of the user at the particular point of entry.

18. The system of claim 15, wherein the safe entry verification computer device at a particular point of entry is further configured to send a confirming SMS text.

19. The system of claim 15, wherein the safe entry verification computer device at a particular point of entry is further configured to deny access to the area of congregation through the particular point of entry when the result of the medical condition analysis does not meet an entry requirement and to grant access to the area of congregation through the particular point of entry when the result of the medical condition analysis meets the entry requirement.

20. The system of claim 19, wherein the medical condition analysis is a pathogen test and the entry requirement is a negative pathogen test.

21. The system of claim 20, wherein the entry requirement is a negative pathogen test within a period of time of entry into the area of congregation.

22. The system of claim 19, wherein the medical condition analysis is a vaccination and the entry requirement is a completed vaccination.

23. The system of claim 19, wherein the medical condition analysis is a test of an attribute of the user.

24. The system of claim 23, wherein the attribute of the user is a genetic marker.

25. The system of claim 19, wherein the medical condition analysis is a test for one of an absence or presence of a disease.

26. The system of claim 19, wherein the safe entry verification computer device at a particular point of entry is further configured to perform a rule-based interpretation of the medical condition analysis result to determine the entry requirement.

27. The system of claim 19, wherein the safe entry verification computer device at a particular point of entry is further configured to verify an identity of the user using identifying information of the user.

28. The system of claim 27, wherein the user identifying information is one of a name of the user, a photograph of the user, a fingerprint of the user and a facial scan of the user.

* * * * *